United States Patent [19]
Tanaka et al.

[11] Patent Number: 6,019,991
[45] Date of Patent: Feb. 1, 2000

[54] TWO-PHASE COSMETIC COMPOSITION

[75] Inventors: Tomoko Tanaka, Norwalk, Conn.; Amy Christine Zimmerman, Grand Rapids, Mich.

[73] Assignee: Chesebrough-Pond's USA Co.,, Greenwich, Conn.

[21] Appl. No.: 09/012,302

[22] Filed: Jan. 23, 1998

[51] Int. Cl.⁷ .............................. A61K 7/00; A61K 7/42; A61K 7/44
[52] U.S. Cl. .............................. 424/401; 424/59; 424/60
[58] Field of Search ................................. 424/401, 59, 60

[56] References Cited

U.S. PATENT DOCUMENTS 5,429,815  7/1995  Faryniarz et al. ........................ 424/47
5,443,817  8/1995  Zimmerman et al. .................... 424/47

*Primary Examiner*—Shelley A. Dodson
*Assistant Examiner*—Marina Lamm
*Attorney, Agent, or Firm*—Milton L. Honig

[57] ABSTRACT

A two-phase cosmetic composition is provided packaged in a clear container. Within the container is an oil and an aqueous phase separated from one another but when shaken form a highly temporary, clear emulsion. One of the phases is colored with a dye while the other is ordinarily water white. Color stability may be enhanced through use of a UV protectant. A bead control agent may be included to eliminate unsightly bead formation on walls of the container. Sorbitan derivatives are useful for this purpose.

10 Claims, No Drawings

TWO-PHASE COSMETIC COMPOSITION

BACKGROUND OF THE INVENTION

1. Field of the Invention

The invention concerns a cosmetic composition, especially a facial toner, with unusual visual aesthetics.

2. The Related Art

Most cosmetic liquid compositions are single phase formulations. Even when these liquids are combinations of oil and water, substantial efforts are directed at providing an emulsion wherein the components do not separate from one another. By contrast, the art has viewed two-phase systems as being aesthetically and functionally deficient. Normally emulsifiers and coupling agents are formulated into the oil and water formulation to ensure stable emulsification.

Illustrative of the prejudice against separation of phases are U.S. Pat. No. 5,429,815 (Faryniarz et al.) and U.S. Pat. No. 5,443,817 (Zimmerman et al.). These documents describe sprayable cosmetic compositions in a clear bottle wherein great effort is applied to achieve a single-phase fluid despite the presence of a propellant system which is difficulty miscible with the aqueous cleansing concentrate.

New product forms are constantly being sought. These forms should have visual characteristics so they can be distinguished from competitive products. These should be elegant in their physical presentation while effective in their performance activity.

Accordingly, it is an object of the present invention to provide a cosmetic composition, especially a toner, with a strikingly different visual format.

Another object of the present invention is to provide a clear cosmetic composition, especially a toner, in a clear container.

Still a further object of the present invention is to provide a cosmetic composition that beyond aesthetic appeal also functions to clean and serves as an astringent when applied to facial areas.

These and other objects of the present invention will become more readily apparent from the description and examples which follow.

SUMMARY OF THE INVENTION

A cosmetic product is provided including:

(A) a container with a clear wall for viewing contents thereof; and
(B) a two-phase cosmetic composition including:
   (i) an oil phase;
   (ii) an aqueous phase, the oil and aqueous phases being separate from one another along a single interface; and
   (iii) an effective amount of a bead control agent present in an amount to remove beads which may form along the interface or walls of the container.

DETAILED DESCRIPTION OF THE INVENTION

Now there has been developed a two-phase oil and water cosmetic composition of unusual visual effect. By the term "two-phase" is meant a separated layer of oil and aqueous phases bounded by a single interface dividing the two phase portions. Further, the term is meant to describe separated layers which upon agitation form a temporary emulsion visually seen as a single phase but separating within four hours, preferably within one hour, more preferably within fifteen minutes, optimally within less than five minutes reverting to the two-phase non-emulsion format.

Amounts of the aqueous and oil phase will range in volume from 5:1 to 1:5, preferably 2:1 to 1:2, optimally about 1:1.

Enhancement of a visual effect is achieved by employing a colorant for at least one of the two-phases. Colors may include red, yellow, blue, green as well as shades therebetween. Red, pink and violet dyes are preferred. Illustrative are Red No. 4, Red No. 40 and the FD&C colorants Red No. 3, Red No. 6, Red No. 28, Red No. 33, Blue No. 1, Green No. 5, Yellow No. 5, all the foregoing being water soluble. Oil soluble dyes may also be utilized such as Green No. 6 and D&C Violet No. 2. Particularly preferred for the present invention is D&C Violet No. 2. Thus, in the preferred embodiment the oil phase will be a deep violet-purple, the aqueous phase colorless and when agitated the combination being violet in visual effect. Active levels of these colorants may range from 0.0001 to about 1%, preferably from 0.001 to 0.1% by weight of a respective phase.

The oil phase may be formed by hydrocarbons, silicones, synthetic or natural esters and combinations thereof. Amounts of any particular oil may range from 1 to 90%, preferably from 10 to 60%, optimally from 15 to 25% by weight of the oil phase.

Hydrocarbons may be in the form of mineral oil, terpenes (such as squalene), isoparaffins and petroleum jelly.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms. Linear volatile silicone materials generally have viscosities less than about 5 centistokes at 25° C. while cyclic materials typically have viscosities of less than about 10 centistokes. Examples of commercially available volatile silicone oils are Dow Corning® 244, 245, 344 and Dow Corning® 345.

Nonvolatile silicone oils include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile silicone oils of the present compositions are the polydimethyl siloxanes having viscosities from about 10 to about 400 centistokes at 25° C.

Silicone copolyols may be employed. Preferred is Dow Corning® 3225C fluid, a mixture of cyclomethicone and dimethicone copolyol having viscosity at 25° C. of 600–2000 cps and a specific gravity of about 0.963.

Among the Esters are:

(1) Alkenyl or alkyl esters of fatty acids having 10 to 20 carbon atoms. Examples thereof include isoarachidyl neopentanoate, isononyl isononanoate, oleyl myristate, oleyl stearate, octyl stearate and oleyl oleate.
(2) Ether-esters such as fatty acid esters of ethoxylated fatty alcohols.
(3) Polyhydric alcohol esters.

(4) Wax esters such as beeswax, spermaceti, myristyl myristate, stearyl stearate.

(5) Mono-, Di- and Triglyceride esters such as PEG-8 caprylic/capric triglyceride.

(6) Sterols esters, of which cholesterol fatty acid esters are examples thereof.

The aqueous phase will usually include water as a major component. Amounts of water may range from 10 to 99%, preferably from 20 to 90%, optimally from 30 to 70% by weight of the aqueous phase.

Other liquid constituents of the aqueous phase may be monohydric and polyhydric alcohols. These may range from 1 to 99%, preferably from 10 to 90%, optimally from 30 to 70% by weight of the aqueous phase. Among suitable monohydric alcohols are ethanol, isopropanol, butanol, hexanol and combinations thereof. Most preferred is ethanol. Suitable polyhydric alcohols include glycerin (known also as glycerol), propylene glycol, dipropylene glycol, polyethylene glycol, sorbitol, hydroxypropyl sorbitol, hexylene glycol, 1,3-butylene glycol, isopropylene glycol and mixtures thereof.

Water soluble compounds may also be included in the aqueous phase. These may include $C_1$–$C_{20}$ alpha- and beta-hydroxycarboxylic acids and salts thereof. The salts are preferably alkalimetal, ammonium and $C_1$–$C_{12}$ alkanolammonium salts. Illustrative acids are glycolic acid, lactic acid and 2-hydroxycaprylic acid. Most preferred is a combination of glycolic and 2-hydroxycaprylic acids and their ammonium salts. Salicylic acid and its salts are also preferably included. Levels of these materials may range from 0.001 to 15%, preferably from 0.1 to 9%, optimally between 0.5 and 7% by weight of the total composition.

Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are disodium EDTA, phenoxyethanol, methyl paraben, propyl paraben, imidazolidinyl urea (commercially available as Germall 1157), sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be present in the cosmetic compositions. These ingredients include vitamins (such as Vitamin $B_6$, Vitamin C, ascorbyl palmitate, Vitamin A palmitate, Vitamin E acetate, biotin, niacin and DL-panthenol), amino acids (such as glycine and serine), ceramides (such as Ceramide I and Ceramide III), bio-hyaluronic acid (with oligosaccharides, available as Actiglide J® from Active Organics US) and sodium PCA.

Fragrances may also be included in either the oil or aqueous phases. Amounts of the fragrance may range from 0.001 to 5%, preferably from 0.05 to 1% by weight of the total composition.

Small amounts of surfactant are necessary in the composition of this invention to emulsify the oil and aqueous phase to achieve temporary emulsion. Amounts of surfactant must however be small enough to avoid compromising the clarity of the phases when in their normal separated state. Amounts of surfactant may range from 0.001 to 2%, preferably from 0.01 to 0.8%, optimally from 0.1 to 0.3% by weight of the total composition. Alkoxylated nonionics are suitable for this purpose. Among these materials are polyoxyethylene-polyoxypropylene surfactants commercially available under the Pluronic® and Tetronic® designations commercially available from the BASF Corporation. Mixtures of Pluronic® L-62 and Tetronic® 304 in ratios of 10:1 to 1:10, preferably about 1:1 may be employed for the present invention.

Buffers can also be included in compositions of the present invention. These buffers normally will be salts and therefore soluble within the aqueous phase. Suitable buffers include the alkali metal salts of citrate, phosphate, borate, tartrate and combinations thereof. Amounts of the buffer may range from 0.01 to 3%, preferably from 0.1 to 2%, optimally from 0.2 to 1% by weight of the total composition.

Color stability may be a problem in certain compositions of the present invention. This is especially so since packaging is preferably transparent which allows a consumer to view the product composition. Sunlight can over time destroy the colorant. For these purposes, it has been found useful to incorporate a UV protectant, particularly a substance absorbing ultraviolet radiation within the range of 290 to 400 nm. Sulfonic acid functionalized chromophoric organic groups are particularly preferred. Illustrative of this category is phenylbenzimidazole sulfonic acid, available commercially as Parsol HS®. Amounts of the protectant may range from 0.01 to 3%, preferably from 0.1 to 2%, optimally from 0.5 to 1.5% by weight of the total composition.

Beyond the requirements of good clarity and color stability, there has also been encountered the problem of beading. Oil droplets or beads have a tendency to cling to part of the container on walls near the water phase. Beads are aesthetically unattractive. Control of the beading phenomena can be achieved by the addition of polyoxyalkylene sorbitan fatty acids. Particularly suitable is POE (20) sorbitan monooleate commercially available as Tween 80®. Amounts of the bead control agent may range from 0.001 to 0.1%, preferably from 0.005 to 0.05%, optimally about 0.01% by weight of the total composition.

An important aspect of the present invention is that the container for the two-phase cosmetic composition be a clear bottle so as to allow viewing of the unusual physical aesthetics of the liquid chemical system. The bottle may be glass or a plastic such as polyvinyl chloride. The composition may be dispensed through a screw-cap opening or delivered via a pump mechanism.

The following examples will more fully illustrate embodiments of this invention. All parts, percentages and proportions referred to herein and in the appended claims are by weight of the total composition unless otherwise indicated.

EXAMPLES 1–8

The following formulations are representative of two-phase cosmetic compositions according to the present invention.

TABLE I

| COMPONENTS | EXAMPLE | | | | | | | |
|---|---|---|---|---|---|---|---|---|
|  | 1 | 2 | 3 | 4 | 5 | 6 | 7 | 8 |
| Oil Phase |  |  |  |  |  |  |  |  |
| Cyctomethicone (DC 245) | 20 | 20 | 20 | 20 | 20 | 20 | 20 | 20 |
| Dimethicone (DC 200) 65 cst | 5 | 5 | 5 | 5 | 5 | 5 | 5 | 5 |
| Vitamin E Acetate | 0.05 | 0.05 | 0.05 | 0.05 | 0.05 | 0.05 | 0.05 | 0.05 |
| D&C Violet No. 2 (0.1% in DC 245) | 0.1 | 0.1 | 0.1 | 0.1 | 0.1 | 0.1 | 0.1 | 0.1 |
| Aqueous Phase (B) |  |  |  |  |  |  |  |  |
| Water | 36.63 | 38.63 | 37.88 | 37.88 | 37.88 | 37.43 | 37.43 | 38.13 |
| Parsol HS ® | 1.00 | 2.00 | 1.25 | 1.25 | 1.25 | 0.80 | 0.80 | 1.50 |
| Glycerin | 1 | 1 | 1 | 1 | 1 | 1 | 1 | 1 |
| Sodium Citrate | 1 | 1 | 1 | 1 | 1 | 1 | 1 | 1 |
| DL-Panthenol | 0.1 | 0.1 | 0.1 | 0.1 | 0.1 | 0.1 | 0.1 | 0.1 |
| Tetronic 304 ® | 0.095 | 0.095 | 0.095 | 0.095 | 0.095 | 0.095 | 0.095 | 0.095 |
| Pluronic 62 ® | 0.095 | 0.05 | 0.095 | 0.095 | 0.095 | 0.095 | 0.095 | 0.095 |
| Disodium EDTA | 0.05 | 0.05 | 0.05 | 0.05 | 0.05 | 0.05 | 0.05 | 0.05 |
| Aqueous Phase (B') |  |  |  |  |  |  |  |  |
| Water | 5 | 5 | 5 | 5 | 5 | 5 | 5 | 5 |
| Glycolic Acid (70% active) | 1.44 | 1.44 | 1.44 | 1.44 | 1.44 | 1.44 | 1.44 | 1.44 |
| Ammonia (Aqua 26BE) | 1.35 | 1.35 | 1.35 | 1.35 | 1.35 | 1.35 | 1.35 | 1.35 |
| Aqueous Phase (B") |  |  |  |  |  |  |  |  |
| Water | 5.0 | 5.0 | 5.0 | 4.9 | 4.5 | 4.9 | 4.8 | 4.9 |
| Alcohol SDA 40 B | 20 | 20 | 20 | 20 | 20 | 20 | 20 | 20 |
| Salicylic Acid | 0.5 | 0.5 | 0.5 | 0.5 | 0.5 | 0.5 | 0.5 | 0.5 |
| Fragrance | 0.075 | 0.075 | 0.075 | 0.075 | 0.075 | 0.075 | 0.075 | 0.075 |
| Tween 80 ® | 0.01 | 0.01 | 0.01 | 0.1 | 0.5 | 0.1 | 0.2 | 0.1 |
| Hydroxycaprylic Acid | 0.005 | 0.005 | 0.005 | 0.005 | 0.005 | 0.005 | 0.005 | 0.005 |

The formulas in Table I are prepared by separately forming the oil phase and the aqueous phases B, B' and B". Aqueous phase B' is added to B with stirring. Subsequently aqueous phase B" is added to the previous combined aqueous phases B, B'. Finally, the oil phase is added to the combination of aqueous phases B, B' and B".

EXAMPLE 9

A series of experiments were conducted to evaluate the effect of Tween 80® on the formation of beads along walls of a transparent (clear) container. First a base formula was prepared as shown in Table II.

TABLE II

| COMPONENTS | EXAMPLE |
|---|---|
| Oil Phase |  |
| Cyclomethicone (DC 245) | 20 |
| Dimethicone (DC 200) 65 cst | 5 |
| Vitamin E Acetate | 0.05 |
| D&C Violet No. 2 (0.1% in DC 245) | 0.1 |
| Aqueous Phase (B) |  |
| Water | 37.88 |
| Parsol HS ® | 1.25 |
| Glycerin | 1 |
| Sodium Citrate | 1 |
| DL-Panthenol | 0.1 |
| Disodium EDTA | 0.05 |

TABLE II-continued

| COMPONENTS | EXAMPLE |
|---|---|
| Aqueous Phase (B') |  |
| Water | 5 |
| Glycolic Acid (70% active) | 1.44 |
| Ammonia (Aqua 26BE) | 1.35 |
| Aqueous Phase (B") |  |
| Water | 5.0 |
| Alcohol SDA 40 B | 20 |
| Salicylic Acid | 0.5 |
| Fragrance | 0.075 |
| Hydroxycaprylic Acid | 0.005 |

The results of physical property testing with the above base and variations in the amount of Tween 80® are reported under Table III.

TABLE III

| | EXAMPLE (WT. %) | | | | |
|---|---|---|---|---|---|
| | 9 (Control) | 9A | 9B | 9C | 9D |
| Tetronic 304 | 0.1% | 0.975% | 0.095% | 0.0925% | 0.09% |
| Pluronic L-62 | 0.1% | 0.975% | 0.095% | 0.0925% | 0.09% |
| Tween 80 | 0 | 0.005% | 0.01% | 0.015% | 0.02% |
| Overnight/PVC | | | | | |
| 4° C. | beads | w/p:beads less than control o/p:beads much less visible than control | w/p:a few small beads o/p:beads much less visible than control | w/p:a few small beads o/p:beads much less visible than control, only thin layer (interface) | w/p:a few small beads o/p:beads much less visible than control, only thin layer (interface) |
| 22° C. | beads | w/p:beads less than control o/p:beads much less visible than control | w/p:a few small beads o/p:beads much less visible than control | w/p:a few small beads o/p:beads much less visible than control, only thin layer (interface) | w/p:a few small beads o/p:beads much less visible than control, only thin layer (interface) |
| Several shakes/PVC | beads | w/p:beads | w/p:a few | w/p:a few | w/p:a few |
| 4° C. | | less than control o/p:beads much less visible than control | small beads o/p:beads much less visible than control | small beads op:beads much less visible than control | small beads o/p:beads much less visible than control |
| 22° C. | beads | w/p:beads less than control o/p:beads much less visible than control | w/p:a few small beads o/p:beads much less visible than control | w/p:a few small beads o/p:beads much less visible than control | w/p:a few small beads o/p:beads much less visible than control |
| 1 week/several shakes/PVC | | | | | |
| 4° C. | beads | w/p:beads less than control o/p:beads much less visible than control | w/p:no beads o/p:beads much less visible than control | w/p:no beads o/p:beads much less visible than control | w/p:no beads o/p:beads much less visible than control |
| 22° C. | beads | w/p:beads less than control o/p:beads much less visible than control | w/p:no beads o/p:beads much less visible than control | w/p:no beads o/p:beads much less visible than control | w/p:no beads o/p:beads much less visible than control |
| Vigorous shake 1 week 4° C. | beads hazy | some small beads near interface; hazy | w/o:no beads o/p-beads (much less visible than control); hazy | w/p:no beads o/p:beads (much less visible than control); hazy | w/p:no beads o/p:beads (much less visible than control); hazy very white milky layer |

Footnote:
w/p indicates aqueous phase
o/p indicates oil phase

EXAMPLE 10

A series of experiments were conducted to evaluate the effects of different types of UV protectants. these were formulated in the base formula of Table II except that Parsol HS® was replaced successively by each of the following UV protectants. Parsol MCX (Octyl Mthoxycinnamate) Parsol HS (Phenylbenzimidazole Sulfonic Acid) Escalol 507 (Octyl Dimethyl PABA) Escalol 587 (Octyl Salicylate) Escalol 597 (Octocrylate) Neo Heliopnan TS (Triethyanolamine Salicylate) Eusolex HMS (Homomenthyl Salicylate) Uvinyl M-40 (Benzophenone-3)

Formulations under these experiments were stored at room temperature for a total of three months in a PVC bottle under Summer daylight conditions. Color and stability were checked every month. Clarity was improved by the presence of most of the listed UV protectants but the best performance was obtained with the use of Parsol HS®.

Although this invention has been described with reference to specific Examples, it will be apparent to one skilled in the art that various modifications will be suggested, all of which are within the spirit and purview of this invention.

What is claimed is:

1. A cosmetic product comprising:
    (A) a container with a clear wall for viewing contents thereof; and
    (B) a two-phase cosmetic composition comprising:
        (i) an oil phase;
        (ii) an aqueous phase, the oil and aqueous phases being separate from one another along a single interface;
        (iii) a nonionic bead control agent present in an effective amount to remove beads which may form along the interface or walls of the container;
        (iv) a colored dye present in an effective amount to color at least one of the oil and aqueous phases; and
        (v) a UV protectant which is a sulfonic acid functionalized chromophoric organic material absorbing in the range of 290 to 400 nm.

2. The composition according to claim 1 wherein both phases are clear.

3. The composition according to claim 2 wherein one of the clear phases is water white and the other phase is colored.

4. The composition according to claim 3 wherein the colored dye is violet.

5. The composition according to claim 1 wherein the UV protectant is phenylbenzimidazole sulfonic acid.

6. The composition according to claim 1 further comprising a surfactant in an amount from 0.001 to 2% by weight of the total composition.

7. The composition according to claim 6 wherein the surfactant is present from 0.1 to 0.3% by weight of the total composition.

8. The composition according to claim 1 wherein the bead control agent is a sorbitan compound present in an amount from 0.001 to 0.2% by weight of the total composition.

9. The composition according to claim 8 wherein the sorbitan compound is a polyoxyalkylene sorbitan fatty acid present in an amount from 0.001 to 0.1% by weight of the total composition.

10. The composition according to claim 1 wherein the UV protedtant is present in an amount from 0.01 to 3% by weight of the total composition.

\* \* \* \* \*

UNITED STATES PATENT AND TRADEMARK OFFICE
CERTIFICATE OF CORRECTION

PATENT NO. : 6,019,991
DATED : February 1, 2000
INVENTOR(S) : Tanaka et al.

It is certified that error appears in the above-indentified patent and that said Letters Patent is hereby corrected as shown below:

Title page, item [73],

Assignee change "Chesebrough-Pond's USA Co.," to

-- Chesebrough-Pond's USA Co., Division of Conopco, Inc. --

Signed and Sealed this

Twenty-seventh Day of February, 2001

*Attest:*

NICHOLAS P. GODICI

*Attesting Officer*  *Acting Director of the United States Patent and Trademark Office*